United States Patent [19]

Nakayama et al.

[11] Patent Number: 5,366,985
[45] Date of Patent: Nov. 22, 1994

[54] METHOD FOR PREPARATION OF AN AQUEOUS SUSPENSION

[75] Inventors: Hisayuki Nakayama; Kazumichi Ushio, both of Nishinomiya; Katsuhiro Inada, Osaka, all of Japan

[73] Assignee: Senju Pharmaceutical Co., Ltd., Osaka, Japan

[21] Appl. No.: 946,443

[22] PCT Filed: Jul. 11, 1991

[86] PCT No.: PCT/JP91/00932
§ 371 Date: Nov. 16, 1992
§ 102(e) Date: Nov. 16, 1992

[87] PCT Pub. No.: WO92/17174
PCT Pub. Date: Oct. 15, 1992

[30] Foreign Application Priority Data

Mar. 27, 1991 [JP] Japan .................. 3-062909

[51] Int. Cl.⁵ .......................... A61K 31/425
[52] U.S. Cl. .................. 514/369; 548/183; 514/912
[58] Field of Search ........... 514/369, 912; 548/183

[56] References Cited

U.S. PATENT DOCUMENTS 5,192,535  3/1993  David ................ 424/78.04

Primary Examiner—Robert Gerstl
Attorney, Agent, or Firm—Wenderoth, Lind & Ponack

[57] ABSTRACT

A stable aqueous suspension, which is particularly suitable for eyedrops for the treatment of keratopathy and other diseases, containing 5-(3-ethoxy-4-n-pentyloxyphenyl)thiazolidine-2,4-dione can be prepared by adding an acid to an aqueous solution containing one or more members selected from the group consisting of polyvinyl alcohol, polyvinylpyrrolidone, hydroxypropylmethylcellulose, methylcellulose and hydroxyethylcellulose and 5-(3-ethoxy-4-n-pentyloxyphenyl)-thiazolidine-2,4-dione and having a pH value of not lower than 8 to adjust said aqueous solution to a pH value of not higher than 7.

9 Claims, No Drawings

METHOD FOR PREPARATION OF AN AQUEOUS SUSPENSION

TECHNICAL FIELD

The present invention relates to a method of preparing a stable aqueous suspension. More particularly, the invention relates to a method of preparing a stable aqueous suspension of 5-(3-ethoxy-4-n-pentyloxyphenyl)-thiazolidine-2,4-dione which is useful for the prevention and treatment of, inter alia, diabetic cataract, keratopathy and diseases of the iris and cilia.

BACKGROUND ART

The active ingredient of the aqueous suspension obtainable by the method of the invention, namely 5-(3-ethoxy-4-n-pentyloxyphenyl)thiazolidine-2,4-dione (hereinafter sometimes referred to briefly as CT-112), is a known compound having aldose reductase inhibitory activity. It has been demonstrated that this compound exerts prophylactic and therapeutic effects on chronic symptoms of diabetic cataract, neuropathy and retinopathy in mammals inclusive of man (Japanese Kokai Patent Application No. 57-28075) and therapeutic efficacy in diseases of the iris and cilia (Japanese Kokai Patent Application No. 61-43114).

When an aqueous preparation of CT-112, such as eyedrops or an injection, is to be manufactured for the treatment or prevention of the above-mentioned diseases, it is necessary to suspend the compound in water because CT-112 is only sparingly soluble in water over the pH range which is acceptable for a topical drug or an injection.

However, if such an aqueous suspension is prepared by the conventional pharmaceutical procedure, for example by dispersing the bulk powder of CT-112 directly in water or dissolving it in an appropriate solvent and, then, processing the solution into an aqueous suspension, the resulting aggregation of CT-112 or entrapment thereof in foams in the course of manufacture or adsorption of CT-112 on the container wall will lead to decreases in content and poor dispersion, thus making it extremely difficult to provide a stable aqueous CT-112 suspension.

Accordingly the inventors of the present invention explored into this field of technology for overcoming the above-mentioned drawbacks and found surprisingly that a stable aqueous suspension free from the above disadvantages can be successfully prepared by providing an aqueous solution of CT-112 whose pH has been previously adjusted to a certain value and then adjusting the pH of said aqueous solution in the presence of a defined water-soluble macromolecular compound.

DISCLOSURE OF THE INVENTION

The present invention is directed to:
1. a method of preparing an aqueous suspension of finely divided 5-(3-ethoxy-4-n-pentyloxyphenyl)-thiazolidine-2,4-dione characterized by adding an acid to an aqueous solution prepared by dissolving one or more members selected from the water-soluble macromolecular compound group consisting of polyvinyl alcohol, polyvinylpyrrolidone, hydroxypropylmethylcellulose, methylcellulose and hydroxyethylcellulose and 5-(3-ethoxy-4-n-pentyloxyphenyl)thiazolidine-2,4-dione in water and having a pH value of not lower than 8 to adjust said aqueous solution to a pH value not higher than 7 and
2. an aqueous ophthalmic preparation for topical application which is a suspension of finely divided 5-(3-ethoxy-4-n-pentyloxyphenyl)thiazolidine-2,4-dione having a particle diameter of not greater than 10 μm.

5-(3-Ethoxy-4-n-pentyloxyphenyl)thiazolidine-2,4-dione (CT-112), which is used as the active ingredient of the aqueous suspension of the invention, can be synthesized by the process described in Japanese Kokai Patent Application No. 57-28075 or any relevant process analogous thereto. CT-112, which can be used in the preparation of an aqueous suspension of the present invention, may be the free compound or an alkali metal salt thereof, such as the sodium salt, the potassium salt or the like.

Preparation of an aqueous suspension according to the present invention can be carried out in the following manner. First, an aqueous solution having a pH value of not lower than 8 is prepared from one or more members selected from the group consisting of polyvinyl alcohol, polyvinylpyrrolidone, hydroxypropylmethylcellulose, methylcellulose and hydroxyethylcellulose (hereinafter sometimes referred to collectively as a water-soluble macromolecular compound) and CT-112.

This preparation of an aqueous solution can be carried out by mixing or dissolving CT-112 and a water-soluble macromolecular compound in water and, then, adjusting the pH of the solution or alternatively by adding either one of said ingredients to water, adjusting the pH of the solution and, then, adding and dissolving the other ingredient. It is also possible to dissolve CT-112 and said water-soluble macromolecular compound in an aqueous medium whose pH has been previously adjusted as required. The timing of addition of CT-112 and said water-soluble macromolecular compound may be optionally concurrent or staggered and, in the latter case, whichever may occur first. This dissolution procedure is preferably performed as quickly as possible to avoid decomposition of CT-112. The water-soluble macromolecular compound may be provided as previously dissolved in water, whereby the whole dissolution time can be curtailed.

Of the water-soluble macromolecular compounds mentioned above, the most preferred is hydroxypropylmethylcellulose. According to necessity and the intended application, the water-soluble macromolecular compounds mentioned above can be used in an appropriate combination. When two or more different water-soluble macromolecular compounds are used in combination, the combinations of, for example, hydroxypropylmethylcellulose-polyvinylpyrrolidone, hydroxypropylmethylcellulose-polyvinyl alcohol, and hydroxypropylmethylcellulose-hydroxyethylcellulose are preferred. Where necessary, the specified water-soluble macromolecular compounds of the present invention may be used in combination with other water-soluble macromolecular compounds such as polyethylene glycol, carboxymethylcellulose sodium and so on.

The pH of the aqueous solution is not lower than 8 and preferably between 10 and 13. Any pH value in excess of the above range is undesirable, for it may induce decomposition of CT-112. On the alkaline side, i.e. at a pH less than 8, it takes an objectionably long time to dissolve CT-112.

The concentration of CT-112 in the solution is generally not less than 0.5 w/w % and preferably 2 to 5 w/w %.

The concentration of the water-soluble macromolecular compound is generally 0.1 to 10 w/w % and preferably 0.5 to 5 w/w %.

The adjustment of pH is carried out by adding an alkaline compound. The alkaline compound just mentioned includes not only bases such as sodium hydroxide, potassium hydroxide, etc. but also salts which dissolve in water to give alkaline solutions, such as borax, sodium carbonate, trisodium phosphate, trisodium citrate and so on.

While the aqueous solution thus obtained is stirred, an acid is gradually added so as to adjust the solution to a pH not more than 7, preferably between about 4 to about 6, whereby CT-112 is crystallized to give an aqueous suspension. The stirring is preferably gentle enough to avoid foaming so that CT-112 will not be entrapped in the foams. The acid mentioned just above includes not only a variety of acids, such as hydrochloric acid, sulfuric acid, acetic acid, phosphoric acid, etc., but also those compounds which dissolve in water to give acidic solutions, such as monosodium phosphate, monosodium citrate and so on.

The particles of CT-112 in the resulting suspension are uniform in size and not more than 10 μm. Moreover, the crystals are hydrophilic and stable in water. Therefore, this aqueous suspension is very stable. Moreover, since uniformly fine particles can be easily formed in the present invention by adjusting the kind and/or concentration of water-soluble macromolecular compound, the suspension can be sterilized by filtration and since this means that it is no longer necessary to use sterile raw materials, a stable aqueous suspension can be provided with great advantage.

The aqueous suspension prepared by the method of the present invention can be used, either as it is or after adjustment of concentration with purified water or/and, where necessary, addition of other additive, as an ophthalmic drug for topical application, an injection or the like.

The proper concentration of CT-112 in the aqueous suspension is dependent on the type of disease to be managed, the severity of clinical condition, the patient's age and body weight, the method of administration, etc., but it is generally advisable to use CT-112 in a concentration of generally 0.01 to 5 w/w % and preferably about 0.05 to 1 w/w %.

While the concentration of said water-soluble macromolecular compound in the aqueous suspension is dependent on the concentration of CT-112 to be dispersed, the kind and molecular weight of water-soluble macromolecular compound, etc., it is advisable to use such a compound in a concentration of generally 0.001 to 10 w/w % and preferably 0.02 to 0.5 w/w %.

In the aqueous suspension provided by the method of the invention, there may be incorporated, where necessary and unless contrary to the objects of the invention, other pharmacologically active compounds of the sine type or of different types.

When the aqueous suspension is to be used as an ophthalmic drug for instillation, there may be incorporated therein various additives which are commonly used in topical ophthalmic preparations, such as buffers, isotonizing agents [e.g. boric acid, salts (sodium chloride, etc.), glycerin, sugars, etc.] and preservatives (e.g. benzalkonium chloride, benzethonium chloride, cetylpiperidinium chloride, chlorobutanol, p-hydroxybenzoic esters, etc.). Each of these additives can be used either singly or in a combination of two or more species. The proportions of such additives in the final ophthalmic preparation may be 0.05 to 2 w/w % for buffers, generally not more than about 5 w/w % for isotonizing agents, and about 0.001 to 0.5 w/w % for preservatives.

The method of preparing an aqueous suspension according to the present invention provides an aqueous suspension in which CT-112 is uniformly dispersed as fine particles not larger the 10 μm and which remains stable for a long period of time without giving foreign body sensation. Therefore, the aqueous suspension of the present invention can be used to great advantage in the prevention and treatment of, inter alia, diabetic cataract, retinopathy, and diseases of the iris and cilia.

Best Mode for Carrying Out the Invention

The following experimental and working examples are further illustrative of the present invention.

EXPERIMENTAL EXAMPLE 1

Study of Dispersing Agents (1) Method

In 100 ml of sterile purified water were dissolved 1 g of sodium hydroxide and 5 g of 5-(3-ethoxy-4-n-pentyloxyphenyl)thiazolidine-2,4-dione, followed by addition of 500 ml of one of the dispersing agents shown in Table 1. While this solution was stirred, 8N hydrochloric acid was added dropwise to adjust the solution to pH 5.5. This solution was examined under the microscope.

TABLE 1

| Dispersing agent | concentration (w/w %) |
| --- | --- |
| Polysorbate | 0.1 |
| HCO-60 | 0.1 |
| Glycerin | 1.4 |
| HPMC | 0.2 |
| PVP | 2.0 |
| PVA | 2.0 |
| HEC | 0.2 |
| MC | 0.2 |

HCO-60 ... Polyoxyethylene-hydrogenated caster oil
HPMC ... Hydroxypropylmethylcellulose
PVP ... Polyvinylpyrrolidone
PVA ... Polyvinyl alcohol
HEC ... Hydroxyethylcellulose
HC ... Methylcellulose (2) Results It was found that whereas dispersed crystals of the active compound were square in configuration and hydrophobic when polysorbate 80, HCO-60 or glycerin was used as the dispersing agent, they were amorphous and hydrophilic when the dispersing agent was hydroxypropylmethylcellulose, polyvinylpyrrolidone, polyvinyl alcohol, hydroxyethylcellulose or methylcellulose. The above results indicate that the water-soluble macromolecular compounds, namely hydroxypropylmethylcellulose, polyvinylpyrrolidone, polyvinyl alcohol, hydroxyethylcellulose and methylcellulose, are useful dispersing agents according to the invention.

EXPERIMENTAL EXAMPLE 2

Stability test (1) Method

The composition shown in Table 2 was filled into 5 ml polypropylene containers and allowed to stand at 4° C., 15° C., 25° C., 30° C., 40° C. and 50° C. After 2 months, these samples were examined for crystallinity and aggregation and the particle diameters were measured.

The above composition was prepared in the following manner. Thus, HPMC, sodium hydroxide and the active compound (CT-112) were thoroughly dissolved in about 10 ml of purified water and the solution was filtered through a bacterial filter. The pH of this solution was 12.2. While this solution was stirred, hydrochloric acid was gradually added dropwise so as to adjust the solution to pH 5.5. To this solution was added 70 ml of a solution prepared by dissolving methyl p-hydroxybenzoate, sodium edetate, concentrated glycerin and sodium citrate in water and filtering the solution through a bacterial filter. This mixture was further diluted with purified water to make a total of 100 ml.

TABLE 2

| Formulation | Amount |
| --- | --- |
| Active compound (CT-112) | 0.5 g |
| HPMC | 0.1 g |
| Methyl-p-hydroxybenzoate | 0.025 g |
| Sodium edetate | 0.01 g |
| Concentrated glycerin | 1.9 g |
| Sodium citrate | 0.05 g |
| Sodium hydroxide | 0.1 g |
| Hydrochloric acid | q.s. |
| Sterile purified water | q.s. |
| Total | 100 ml |

(2) Results

At any of the temperatures mentioned above, the active compound remained uniformly dispersed, without undergoing blocking, even after 2 months. It was thus clear that the above composition does not easily undergo aggregation and remains stable for a long period of time.

EXPERIMENTAL EXAMPLE 3

Stability According to Additives

The stabilizing effects of various additives on the active compound were investigated. First, a composition was prepared by adding 10 ml of purified water containing one of the following additives to 10 ml of a two-fold concentrate of the composition shown in Table 2.

TABLE 3

| | Additives and concentrations |
| --- | --- |
| Additive | Level of addition (w/w %) |
| PVP | 0.2, 0.5, 1.0 |
| PEG | 0.1, 0.2 |
| HEC | 0.1, 0.2 |
| CMC—Na | 0.1, 0.2 |

PVP . . . Polyvinylpyrrolidone
PEG . . . Polyethylene glycol
HEC . . . Hydroxyethylcellulose
CMC—Na . . . Carboxymethylcellulose sodium (1) Method Each of the above aqueous suspensions was placed in a 5 ml polypropylene container and subjected to a cycle test (5° C.→20° C.→40° C.→30° C., 3 hours cycle). After 40 cycles, the crystal form and dispersed state of the active compound were examined and the particle diameter was measured.

(2) Results

None of the suspensions showed change in crystal form or particle size, indicating that the above additives can be employed.

EXPERIMENTAL EXAMPLE 4

To portions of the composition of Table 2 were added the same additives as used in Experimental Example 3, respectively, and the feeling of use of the resulting ophthalmic preparations was scored according to the evaluation criteria set forth below. The results were as follows.

TABLE 4

| Additive | Irritation score |
| --- | --- |
| None | 0 |
| PVP | 0 |
| PVA | 0 |
| PEG | 0 |
| HEC | 0 |
| CMC—Na | 0 |

Evaluation criteria
4 . . . Very irritating
3 . . . Irritating
2 . . . Slightly irritating
1 . . . Substantially not irritating The above results indicated that none of the preparations caused no irritation.

EXPERIMENTAL EXAMPLE 5

In sterile purified water (X ml in Table 5) were dissolved sodium hydroxide (0.5 g), hydroxypropylmethylcellulose (HPMC) (Y g in Table 5) and CT-112 (1 g) and the solution was filtered through a bacterial filter. While this solution was stirred, 2N hydrochloric acid was gradually added dropwise so as to adjust the solution to pH 5.5. To this solution was added an aqueous solution (80 ml) prepared by dissolving HPMC (Z g in Table 5), methyl p-hydroxybenzoate (0.125 g), sodium edetate (0.05 g), concentrated glycerin (9.5 g) and sodium citrate (0.25 g) and filtering the solution through a bacterial filter. This mixture was further diluted with sterile purified water to make 500 ml. In this manner, preparations a, b and c were provided. The feeling of use of these preparations was scored according to the same evaluation criteria as used in Experimental Example 4. The results were shown in Table 5.

TABLE 5

| | a | b | c |
| --- | --- | --- | --- |
| Purified water (X ml) | 400 | 200 | 40 |
| HPMC (Y g) | 1 | 0.5 | 0.1 |
| HPMC (Z g) | 0 | 0.5 | 0.9 |
| Irritation score | 3 | 0 | 0 |

It was thus clear that when the concentration of CT-112 before addition of the acid is not less than 0.5 w/w %, the resulting ophthalmic preparation is not irritating.

EXAMPLE 1

In about 200 ml of purified water were thoroughly dissolved 0.8 g of sodium hydroxide and 1 g of sodium acetate. Then, 5 g of 5-(3-ethoxy-4-n-pentyloxyphenyl)-thiazolidine-2,4-dione was added and thoroughly dissolved in the above solution. Thereafter, 200 μl of 2.5 w/w % aqueous solution of hydroxypropylmethylcellulose was added and the mixture was filtered through a bacterial filter. The pH of this solution was 11.7. While this solution was stirred, 1N hydrochloric acid was gradually added dropwise to adjust the solution to pH 5. To this solution was added 700 ml of an aqueous solution prepared by dissolving 20 g of concentrated glycerin and 0.3 g of methyl p-hydroxybenzoate and filtering the resulting solution through a bacterial filter, followed by addition of purified water to make 1000 ml.

EXAMPLE 2

In about 10 ml purified water were thoroughly dissolved 2 ml of 1N sodium hydroxide and 0.25 g of 5-(3-ethoxy-4-n-pentyloxyphenyl)thiazolidine-2,4-dione. Then, 10 ml of 10 w/w % polyvinyl alcohol was added and the mixture was filtered through a bacterial filter. The pH of the solution was 11.8. While this solution was stirred, 1 w/w % phosphoric acid was added dropwise to adjust the solution to pH 5.5. To this solution was added 70 ml of an aqueous solution prepared by dissolving 4 g of mannitol and 0.005 g of benzalkonium chloride in water and filtering the resulting solution through a bacterial filter, followed by addition of purified water to make 100 ml.

EXAMPLE 3

To a homogeneous solution composed of 220 μl of 0.2N sodium hydroxide, 5 mg of sodium acetate and 12.5 mg of 5-(3-ethoxy-4-n-pentyloxyphenyl)thiazolidine-2,4-dione was added 200 μl of 25 w/w % aqueous solution of hydroxypropylmethylcellulose and the mixture was filtered through a bacterial filter. The pH of this solution was 11.8. While this solution was stirred, 0.5N hydrochloric acid was gradually added dropwise to adjust the solution to pH 5.5. To this solution was added 3.5 ml of an aqueous solution prepared by adding 1 mg of sodium edetate and filtering the resulting solution through a bacterial filter, followed by addition of purified water to make 5 ml.

We claim:

1. A method for preparing an aqueous suspension of finely divided 5-(3-ethoxy-4-n-pentyloxyphenyl)-thiazolidine-2,4-dione which comprises
   (1) mixing in water
      (a) an alkaline compound,
      (b) at least one water-soluble macromolecular compound selected from the group consisting of polyvinyl alcohol, polyvinylpyrrolidone, hydroxypropylmethylcellulose, methylcellulose and hydroxyethylcellulose, and
      (c) 5-(3-ethoxy-4-n-pentyloxyphenyl)-thiazolidine-2,4-dione
   to form an aqueous solution having a pH value not lower than 8
   (2) adding an acid to said aqueous solution to adjust the pH of said aqueous solution to a value not higher than 7 to thus form said aqueous suspension.

2. A method of preparing an aqueous suspension according to claim 1, wherein the concentrations of the water-soluble macromolecular compound and 5-(3-ethoxy-4-n-pentyloxyphenyl)thiazolidine-2,4-dione in the aqueous suspension, are 0.1 to 10 w/w % and more than 0.5 w/w %, respectively.

3. A method of preparing an aqueous suspension according to claim 1, wherein the chosen water-soluble macromolecular compound is hydroxypropylmethylcellulose.

4. A method of preparing an aqueous suspension according to claim 1, wherein the chosen water-soluble macromolecular compounds are hydroxypropylmethylcellulose and polyvinylpyrrolidone.

5. A method of preparing an aqueous suspension according to claim 1, wherein the chosen water-soluble macromolecular compounds are hydroxypropylmethylcellulose and polyvinyl alcohol.

6. A method of preparing an aqueous suspension according to claim 1, wherein the chosen water-soluble macromolecular compounds are hydroxypropylmethylcellulose and hydroxyethylcellulose.

7. A method of preparing an aqueous suspension according to claim 1, wherein the pH value of the aqueous solution is between 10 and 13.

8. A method of preparing an aqueous suspension according to claim 1, wherein the acid is added dropwise to adjust the solution between pH 4 and 6.

9. An aqueous ophthalmic preparation for topical application having a pH value of not higher than 7 and which comprises an aqueous suspension of finely divided 5-(3-ethoxy 4-n-pentyloxyphenyl)thiazolidine-2,4-dione having a particle diameter of not greater than 10 μm and at least one water-soluble macromolecular compound selected from the group consisting of polyvinyl alcohol, polyvinylpyrrolidone, hydroxypropylmethylcellulose, methylcellulose and hydroxyethylcellulose.

* * * * *